US00PP28645P2

(12) United States Plant Patent
van Sambeek

(10) Patent No.: US PP28,645 P2
(45) Date of Patent: Nov. 14, 2017

(54) ***PHLOX* PLANT NAMED 'BARPHSPHOPI'**

(50) Latin Name: *Phlox subulata*
Varietal Denomination: Barphsphopi

(71) Applicant: Ellen van Sambeek, Aalsmeer (NL)

(72) Inventor: Ellen van Sambeek, Aalsmeer (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/330,227

(22) Filed: Aug. 27, 2016

(51) Int. Cl.
*A01H 5/02* (2006.01)

(52) U.S. Cl.
USPC ..... Plt./320

(58) Field of Classification Search
USPC ..... Plt./320
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Phlox* plant named 'Barphsphopi', characterized by its upright, outwardly spreading and mounding plant habit; vigorous growth habit; early and freely flowering habit; purple violet-colored flowers with dark purple-colored centers; and good garden performance.

1 Drawing Sheet

Botanical designation: *Phlox subulata.*
Cultivar denomination: 'BARPHSPHOPI'.

BACKGROUND OF THE INVENTION

The present invention relates to a new and distinct cultivar of *Phlox* plant, botanically known as *Phlox subulata* and hereinafter referred to by the name 'Barphsphopi'.

The new *Phlox* plant is a product of a planned breeding program conducted by the Inventor in Aalsmeer, The Netherlands. The objective of the breeding program was to create new freely-flowering *Phlox* plants with attractive flower color.

The new *Phlox* plant originated from a self-pollination made by the Inventor in April, 2011 in Aalsmeer, The Netherlands, of a proprietary selection of *Phlox subulata* identified as code number SB-0100, not patented. The new *Phlox* plant was discovered and selected by the Inventor as a single flowering plant from within the progeny of the stated cross-pollination in a controlled environment in Aalsmeer, The Netherlands in April, 2012.

Asexual reproduction of the new *Phlox* plant by cuttings in a controlled environment in Aalsmeer, The Netherlands since June, 2012 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Barphsphopi'. These characteristics in combination distinguish 'Barphsphopi' as a new and distinct *Phlox* plant:

1. Upright, outwardly spreading and mounding plant habit.
2. Vigorous growth habit.
3. Early and freely flowering habit.
4. Purple violet-colored flowers with dark purple-colored centers.
5. Good garden performance.

Plants of the new *Phlox* differ primarily from plants of the parent selection in flower color as plants of the parent selection have soft light pink-colored flowers.

Plants of the new *Phlox* can be compared to plants of *Phlox subulata* 'Emerald Cushion Blue', not patented. In side-by-side comparisons, plants of the new *Phlox* and 'Emerald Cushion Blue' differ in the following characteristics:

1. Plants of the new *Phlox* grow faster than plants of 'Emerald Cushion Blue'.
2. Plants of the new *Phlox* and 'Emerald Cushion Blue' differ in flower color as plants of 'Emerald Cushion Blue' have light violet-colored flowers.
3. Plants of the new *Phlox* are more low-temperature tolerant than plants of 'Emerald Cushion Blue'.

BRIEF DESCRIPTION OF THE PHOTOGRAPH

The accompanying colored photograph illustrates the overall appearance of the new *Phlox* plant showing the colors as true as it is reasonably possible to obtain in colored reproductions of this type. Colors in the photograph may differ slightly from the color values cited in the detailed botanical description which accurately describe the colors of the new *Phlox* plant.

The photograph comprises a side perspective view of typical flowering plant of 'Barphsphopi' grown in a container.

DETAILED BOTANICAL DESCRIPTION

The aforementioned photograph and following observations, measurements and values describe plants grown during the spring in 13-cm containers in an outdoor nursery in Aalsmeer, The Netherlands and under cultural practices typical of commercial *Phlox* production. During the production of the plants, day temperatures averaged 14° C. and night temperatures averaged 5° C. Plants were pinched one time and were ten months old when the photograph and description were taken. In the following description, color references are made to The Royal Horticultural Society Colour Chart, 2001 Edition, except where general terms of ordinary dictionary significance are used.

Botanical classification: *Phlox subulata* 'Barphsphopi'.

Parentage:

*Female, or seed, parent*.—Proprietary selection of *Phlox subulata* identified as code number SB-0100, not patented.

*Male, or pollen, parent*.—Proprietary selection of *Phlox subulata* identified as code number SB-0100, not patented.

Propagation:

*Type*.—By vegetative cuttings.

*Time to initiate roots, summer*.—About 16 days at temperatures about 26° C.

*Time to initiate roots, winter*.—About three weeks at temperatures about 23° C.

*Time to produce a rooted young plant, summer*.—About 24 days at temperatures about 23° C.

*Time to produce a rooted young plant, winter*.—About four weeks at temperatures about 18° C.

*Root description*.—Medium in thickness, fibrous; typically white to light yellow in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial typically grown as a container and garden plant; upright, outwardly spreading and mounding plant habit; vigorous growth habit.

*Plant height*.—About 8 cm.

*Plant width* (*spread*).—About 25 cm.

*Lateral branches*.—Length: About 10 cm. Internode length: About 5 mm. Strength: Moderately strong. Aspect: Upright to outwardly spreading. Texture: Pubescent. Color: Close to 144D; with development, color becoming closer to 153D.

Leaf description:

*Arrangement*.—Opposite, simple; sessile.

*Length*.—About 1.9 cm.

*Width*.—About 2.5 mm.

*Shape*.—Lanceolate.

*Apex*.—Acute.

*Base*.—Truncate.

*Margin*.—Entire, ciliate.

*Texture, upper and lower surfaces*.—Smooth, glabrous.

*Venation pattern*.—Pinnate.

*Color*.—Developing leaves, upper and lower surfaces: Close to 145A. Fully expanded leaves, upper and lower surfaces: Close to 146A; venation, close to 146A.

Flower description:

*Flower type and flowering habit*.—Single rotate and salverform flowers arranged in compound terminal and lateral panicles; flowers face mostly upright to outwardly; freely flowering habit with about 536 flowers developing per plant.

*Fragrance*.—Slightly fragrant, pleasant.

*Natural flowering season*.—Plants begin flowering about 36 weeks after planting; plants begin flowering in April in The Netherlands; flowers persistent.

*Flower buds*.—Height: About 2.2 cm. Diameter: About 4 mm. Shape: Ovoid. Color: Close to 71C.

*Inflorescence height*.—About 7 cm.

*Inflorescence diameter*.—About 5 cm.

*Flower diameter*.—About 2.3 cm.

*Flower depth*.—About 1.5 cm.

*Flower throat diameter*.—About 2 mm.

*Flower tube length*.—About 1.4 cm.

*Flower diameter, proximally*.—About 2 mm.

*Petals*.—Quantity per flower: Typically five in a single whorl; petals fused at the base into a narrow tube. Lobe length: About 1.2 cm. Lobe width: About 1.1 cm. Lobe shape: Obcordate. Lobe apex: Cordate. Lobe margin: Entire. Lobe texture, upper and lower surfaces: Smooth, glabrous. Throat texture: Smooth, glabrous. Tube texture: Smooth, glabrous. Color: When opening, upper surface: Close to 81A; towards the throat, close to 79A. When opening, lower surface: Close to 80B. Fully opened, upper surface: Close to 81A; towards the throat, close to 79A; venation, close to 81A. Fully opened, lower surface: Close to 81B; venation, close to 81B. Throat: Close to 71B; venation, close to 71B. Tube: Close to 71B; venation, close to 71B.

*Sepals*.—Quantity per flower: Typically five in a single whorl, fused towards the base; calyx, campanulate. Length: About 8 mm. Width: About 1 mm. Shape: Narrowly deltoid. Apex: Acuminate. Margin: Entire. Texture, upper surface: Pubescent. Texture, lower surface: Smooth, glabrous. Color: When opening and fully opened, upper surface: Close to 141A. When opening and fully opened, lower surface: Close to 141A.

*Peduncles*.—Length: About 7 cm. Diameter: About 1 mm. Strength: Strong. Texture: Pubescent. Color: Close to 144D.

*Pedicels*.—Length: About 2 cm. Diameter: About 1 mm. Strength: Moderately strong. Texture: Pubescent. Color: Close to 59B.

*Reproductive organs*.—Stamens: Quantity per flower: Typically five. Filament length: About 2 mm. Filament color: Close to 155A. Anther length: About 1.5 mm. Anther color: Close to 15A. Pollen amount: Abundant. Pollen color: Close to 21A. Pistils: Quantity per flower: One. Pistil length: About 1.1 cm. Stigma shape: Cleft, three-parted. Stigma color: Close to 14C. Style length: About 9 mm. Style color: Close to 1D. Ovary color: Close to 141C.

*Seeds and fruits*.—Seed and fruit development have not been observed on plants of the new *Phlox*.

Garden performance: Plants of the new *Phlox* have been observed to have good garden performance and tolerate rain, wind and frost.

Disease & pest resistance: Plants of the new *Phlox* have been observed to be relatively tolerant to Powdery Mildew; plants of the new *Phlox* have not been observed to be resistant to pests and other pathogens common to *Phlox* plants.

It is claimed:

1. A new and distinct *Phlox* plant named 'Barphsphopi' as illustrated and described.

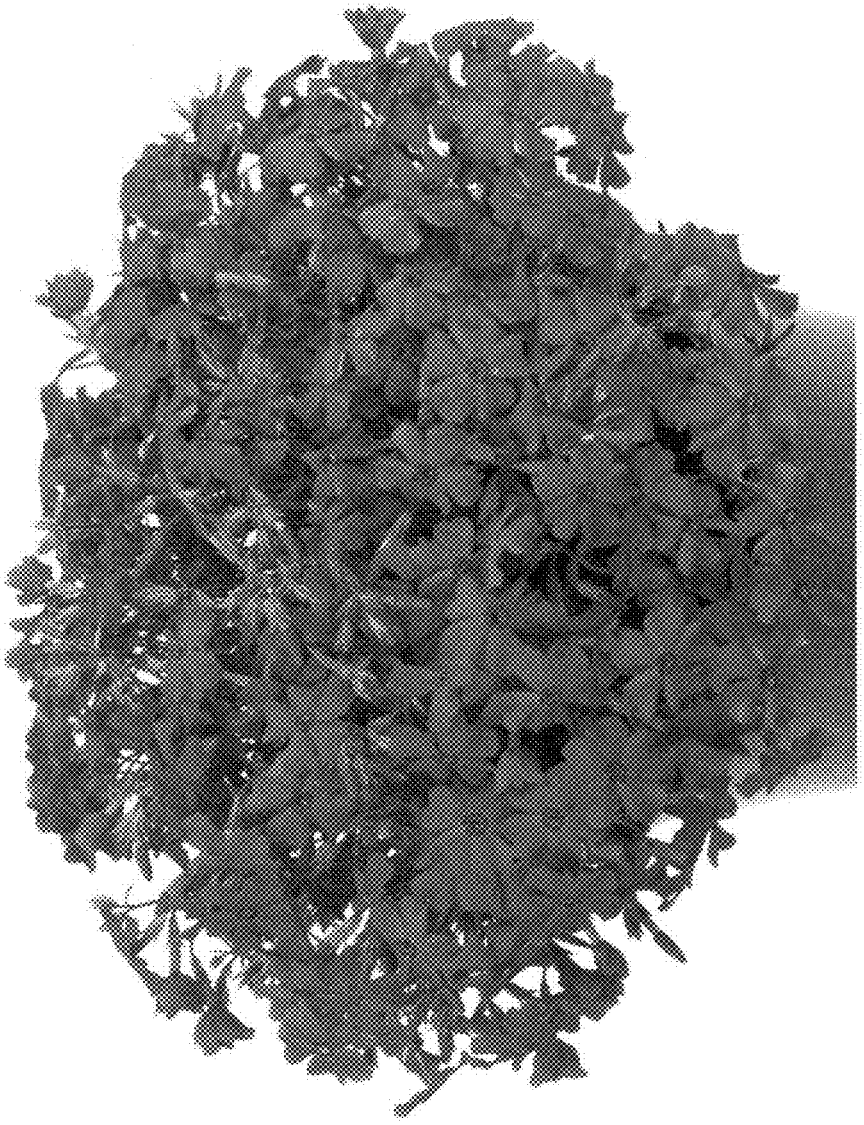

* * * * *